(12) United States Patent
Cao

(10) Patent No.: US 7,928,235 B2
(45) Date of Patent: Apr. 19, 2011

(54) METHODS OF MAKING ESTERS OF CAMPTOTHECINS

(75) Inventor: Zhisong Cao, Friendswood, TX (US)

(73) Assignee: The Christus Stehlin Foundation for Cancer Research, Houston, TX (US)

( * ) Notice: Subject to any disclaimer, the term of this patent is extended or adjusted under 35 U.S.C. 154(b) by 895 days.

(21) Appl. No.: 11/833,031

(22) Filed: Aug. 2, 2007

(65) Prior Publication Data

US 2008/0045717 A1 Feb. 21, 2008

Related U.S. Application Data

(60) Provisional application No. 60/837,437, filed on Aug. 11, 2006.

(51) Int. Cl.
C07D 491/22 (2006.01)
(52) U.S. Cl. .......................................... 546/48; 546/47
(58) Field of Classification Search ................ 546/48, 546/47
See application file for complete search history.

(56) References Cited

U.S. PATENT DOCUMENTS

| | | | |
|---|---|---|---|
| 5,352,789 A | 10/1994 | Hinz | |
| 5,527,913 A | 6/1996 | Hinz | |
| 5,552,154 A | 9/1996 | Giovanella et al. | |
| 5,608,066 A | 3/1997 | Hinz | |
| 5,652,244 A | 7/1997 | Giovanella et al. | |
| 5,731,316 A | 3/1998 | Cao et al. | |
| 5,889,017 A | 3/1999 | Giovanella et al. | |
| 5,922,877 A | 7/1999 | Cao | |
| 5,968,943 A | 10/1999 | Cao et al. | |
| 6,080,751 A | 6/2000 | Stehlin et al. | |
| 6,096,336 A | 8/2000 | Cao et al. | |
| 6,107,486 A | 8/2000 | Hinz | |
| 6,120,793 A | 9/2000 | Cao et al. | |
| 6,156,897 A | 12/2000 | Hinz | |
| 6,166,029 A | 12/2000 | Giovanella et al. | |
| 6,218,399 B1 | 4/2001 | Cao et al. | |
| 6,228,855 B1 | 5/2001 | Cao et al. | |
| 6,342,506 B1 | 1/2002 | Giovanella et al. | |
| 6,352,996 B1 | 3/2002 | Cao et al. | |
| 6,407,118 B1 | 6/2002 | Cao et al. | |
| 6,407,239 B1 | 6/2002 | Cao et al. | |
| 6,624,170 B2 | 9/2003 | Giovanella et al. | |
| RE38,408 E | 1/2004 | Cao | |
| 6,699,875 B2 | 3/2004 | Cao et al. | |
| 6,703,399 B2 | 3/2004 | Cao et al. | |
| 2007/0161668 A1 | 7/2007 | Soon-Shiong et al. | |

FOREIGN PATENT DOCUMENTS

| | | |
|---|---|---|
| WO | WO 97/28165 A1 | 8/1997 |
| WO | WO 98/35940 A1 | 8/1998 |
| WO | WO 03/095461 A1 | 11/2003 |
| WO | WO 2005/062991 A2 | 7/2005 |

OTHER PUBLICATIONS

International Search Report and Written Opinion from the International Patent Application No. PCT/US2007/017295, dated Feb. 22, 2008, eleven pages.

Du et al., "*Semisynthesis of DB-67 and Other Silatecans from Camptothecin by Thiol-Promoted Addition of Silyl Radicals*" Bioorganic & Medicinal Chemistry, 2003, vol. 11, No. 3, pp. 451-458.

U.S. Appl. No. 11/923,727, filed Oct. 25, 2007, Zhisong Cao.

*Primary Examiner* — Charanjit S Aulakh
(74) *Attorney, Agent, or Firm* — Kilyk & Bowersox, P.L.L.C.

(57) ABSTRACT

Methods of preparing CPT-esters are described. The methods include using at least one acid in the esterification reactions or acylation reactions of camptothecins.

11 Claims, No Drawings

METHODS OF MAKING ESTERS OF CAMPTOTHECINS

This application claims the benefit under 35 U.S.C. §119(e) of prior U.S. Provisional Patent Application No. 60/837,437, filed Aug. 11, 2006, which is incorporated in its entirety by reference herein.

FIELD OF THE INVENTION

The present invention relates to methods of making esters of camptothecin.

BACKGROUND OF THE INVENTION

Camptothecin, a cytotoxic alkaloid first isolated from the wood and bark of *Camptotheca Acuminata* (Nyssaceae) by Wall and his coworkers (*J. Am. Chem. Soc.* 88, 3888, 1966), was shown to have antitumor activity against the mouse leukemia L 1210 system. The structure of camptothecin, an alkaloid which has a commonly occurring indole alkaloid group (Heckendorf et al., *J. Org. Chem.* 41, 2045, 1976), is shown below as Formula (X).

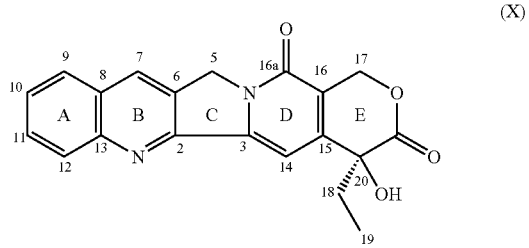

This compound ("CPT") has a pentacyclic ring system with only one asymmetrical center in ring E with a 20(S)-configuration. The pentacyclic ring system includes a pyrrolo [3, 4-b] quinoline moiety (rings A, B and C), a conjugated pyridone (ring D), and a six-membered lactone (ring E) with an α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (*Chem. Rev.* 23, 385, 1973, *Cancer Treat. Rep.* 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al., *Cancer Chemother. Rep.* 54, 461, 1970, and 56, 103, 1972, Muggia et al., *Cancer Chemother. Rep.* 56, 515, 1972, Moertel et al., *Cancer Chemother. Rep.* 56, 95, 1972, and Schaeppi et al., *Cancer Chemother. Rep.* 5:25, 1974). These results caused the discontinuation of phase II trials. Continued evaluation of this agent showed that the sodium carboxylate salt is only 10% as potent as the native camptothecin with the closed lactone ring intact (Wall et al., *In International Symposium on Biochemistry And Physiology of The Alkaloids*, Mothes et al., eds., *Academie—Verlag*, Berlin, 77, 1969, Giovanella et al., *Cancer res.* 51, 3052, 1991). In addition, important parameters for antitumor activity in the camptothecin family have been established (Wall et al., *Ann. Rev., Pharmacol. Toxicol.* 17, 117, 1977). These results indicate that an intact lactone ring E and α-hydroxyl group are essential for antitumor activity.

In 1989, Giovanella et al. found that some of the non-water soluble derivatives of camptothecin have high antitumor activity against xenograft of human tumors (Giovanella et al., *Science*, 246, 1046, 1989). It has also been shown that administration of camptothecin with closed lactone ring is superior to injections of water-soluble carboxylate salt (Giovanella et al., *Cancer Res.*, 51, 3052, 1991). These findings further confirmed the importance of the intact lactone ring to biological activity.

Ring opening of 20(S)-camptothecin ("CPT") leads to much more potent anticancer activity in mice than in humans. In effect, CPT administered intramuscularly ("i.m."), subcutaneously ("s.c."), and intrastomach ("i.s.") has proven to be a very potent anticancer agent against human tumors in mice, i.e., when growing as xenotransplants in nude mice (Giovanella et al., *Cancer Res.* 51:3052, 1991). However, when tumors were treated with CPT in humans, a lower degree of anticancer activity in humans, than in mice, was exhibited (Stehlin et al., *In Camptothecins: New Anticancer Agents*, 1995, CRC Press, pp. 59-65).

The same phenomenon was observed with other CPT-derivatives. In mice, 9-nitrocamptothecin ("9NC") has proven to be 2-3 times more potent than CPT against human tumor xenografts causing the total eradication of all the human malignancies treated (Pantazis et al., *Cancer Res.* 53:1577, 1993; Pantazis et al., *Int. J. Cancer* 53:863, 1995).

Pharmacological studies demonstrated that the majority (57%) of the 9NC drug present in the plasma after i.s. administration is in the closed lactone form. Pharmacological studies on the plasma levels of 9NC after oral administration to Phase I clinical trial patients demonstrate that, on average, only ~3% of the drug present is in the closed lactone form.

In perfect agreement with such findings, the clinical responses in this group of patients, although higher than those obtained with CPT are still a far cry below the results obtained in mice (32/32 complete tumor regressions in mice versus 2/32 in humans). Clearly, there was a pressing need for a modification which will slow and delay the lactone ring opening upon its entrance into the blood circulation.

Ring opening is particularly problematic in that camptothecins exist in two distinct forms at physiological pH, i.e., 7 or above, as shown in the following equilibrium equation:

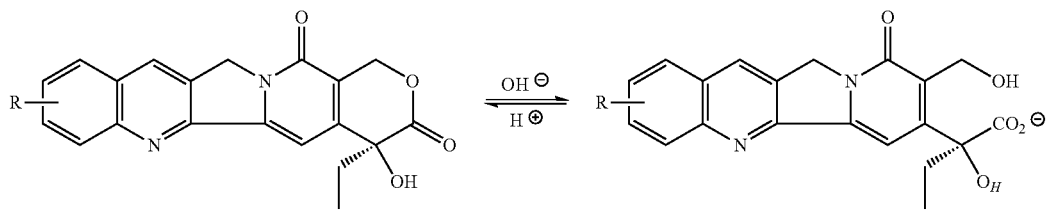

The hydrolysis reaction of the biological active lactone ring of camptothecins with water at higher pH gives the biologically inactive open form. Additionally, the hydrolysis problem with CPT and its analogs is exacerbated in human blood because the predominant human serum albumin (HSA) preferentially binds to the carboxylate form, which shifts the lactone/carboxylate equilibrium toward the inactive form (*J. Biochem.*, 212, 285-287, 1993; *Biochemistry*, 33, 10325-10336, 1994; *Biochemistry*, 33, 12540-12545, 1994). Accordingly, preserving the lactone ring of the molecule for a sufficient time for the tumor cells to cycle through the S-phase is a major challenge and has been the focus of a considerable amount of research.

A number of attempts have been made to provide derivatives of camptothecin having greater biological activity and enhanced stability. Many of these compounds are the products of modifications on the A, B, and C rings of the molecule, but few of these modifications have enhanced the stability of the lactone ring under physiological conditions. Other approaches have been more successful. For instance, acylating of 20-OH group provides a useful tool for the protection of lactone ring E. Wall et al., U.S. Pat. No. 4,943,579, describes several acylated camptothecin compounds having water solubility, although the lactone may not remain intact under physiological conditions. U.S. Pat. No. 5,968,943 to Cao et al. discloses CPT-derivatives which are effective antitumor agents.

A number of different reactions are reported in literature for preparing camptothecin esters.

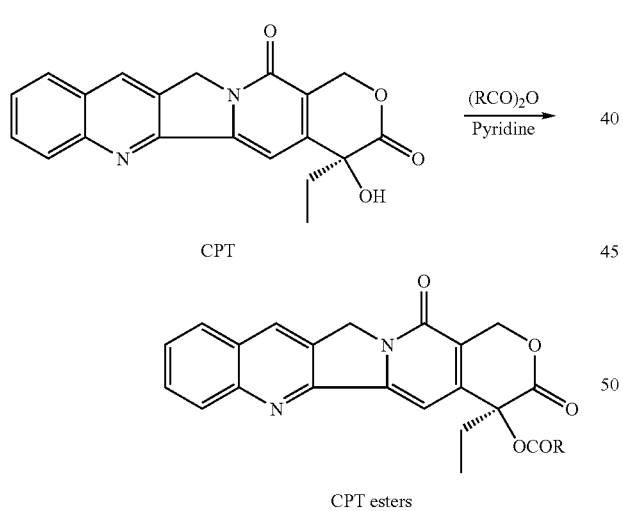

Direct acylation of camptothecin with organic acid anhydrides with pyridine as catalyst was employed for preparing alkyl and alkenyl camptothecin esters (as shown above). This reaction usually gives high yields, but the availability of organic acid anhydrides restricts the scope of the reaction.

A dicyclohexylcarbodiimide (DCC)/dimethylaminopyridine (DMAP) reagent system was therefore, used for acylation reactions of carboxylic acids with alcohols and thiols. Previously, a method was used to prepare aromatic camptothecin esters (as shown below).

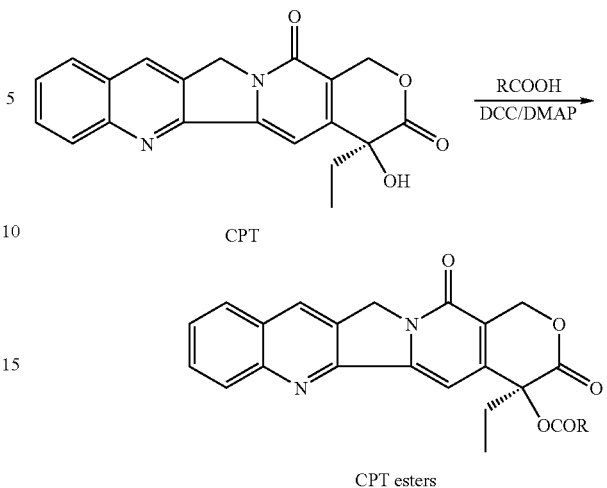

This procedure, however, gives good reaction yields only when the carboxylic acids are very electrophilic. When the acids are less electrophilic, the reaction gives low yield or no expected product at all. For example, when using propionic acid to prepare camptothecin propionate with this procedure, the ester product was essentially not obtained and the starting camptothecin was almost 100% recovered.

Nonanoic chloride was also used as an acylating agent to esterify camptothecin with pyridine as a HCl-trapping agent in methylene chloride. The reaction (as shown below) occurred with low yield (6%).

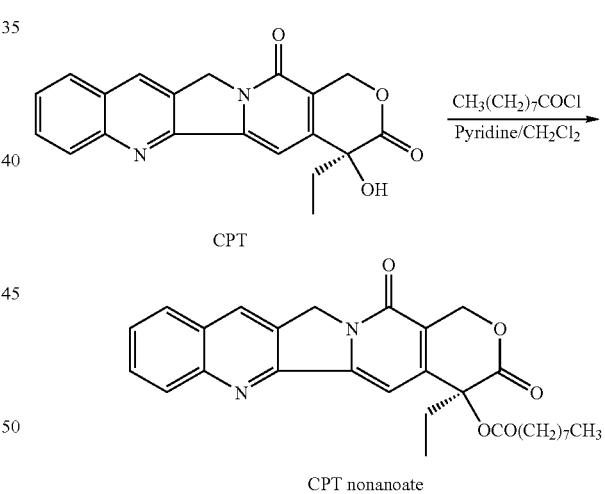

Although there are many methods for preparing camptothecin esters, each procedure has certain restrictions as discussed above. Therefore, there is still a need to develop alternative procedure(s) for preparing camptothecin esters.

SUMMARY OF THE PRESENT INVENTION

Accordingly, it is an object of the present invention to provide less-restrictive new methods to prepare esters of camptothecins.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention, in part, relates to methods for making esters of camptothecin comprising reacting a camptothecin compound with at least one acylating agent protonated by at least one acid.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

All patents, applications, and publications mentioned throughout the application are incorporated in their entirety by reference herein and form a part of the present application.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to methods of making esters of camptothecins. Camptothecins ("CPTs") have considerable anti-tumor and anti-cancer activity, but these compounds are susceptible to degradation under normal physiological conditions, and the metabolites produced often exhibit toxic properties. Therefore, the present invention provides novel methods to prepare CPT derivatives or analogues which preferably remain intact longer in a mammalian body, particularly in the human body, thus enhancing the anti-tumor and anti-cancer effects without producing undesirable side effects.

According to one or more embodiments of the present invention, methods are provided for making aliphatic esters of camptothecin that include the step of reacting a starting camptothecin compound with at least one acylating agent protonated by at least one acid, such as, sulfuric acid. The acylating agent can contain the ester group to be formed on the starting camptothecin. Further details are provided below.

In one or more embodiments, the starting camptothecin reactant compound can be camptothecin or 9-nitrocamptothecin or 9 amino-camptothecin. The starting camptothecin can be a non-ester form of CPT or a CPT derivative and/or can be any CPT compound capable of being esterified.

The starting camptothecin can have the following formula:

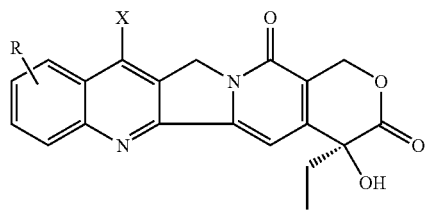

In this formula, the R group represents substituents on one of the rings of the structure above. In particular, R represents H, $NO_2$, $NH_2$, $N_3$, —OH, a halogen (e.g., F, Cl, Br, I), carboxyl (COOH), a $C_{1-16}$ alkyl group, $C_{2-16}$ alkenyl group, a $C_{3-8}$ cycloalkyl group, a $C_{1-8}$ alkoxyl group, an aroxyl group, CN, $SO_3$ H, a $C_{1-8}$ halogenated alkyl group, $(CH_2)_n$ $NR_2^7$ (where $R^7$ can be H, or a $C_{1-8}$ alkyl group, n can be an integer of from 1 to about 8), hydroxyl, SH, $SR^8$ (where $R^8$ can be a $C_{1-8}$ alkyl group, an unsubstituted phenyl group, or a substituted phenyl group), a carbonyl group, (e.g., $COR^9$, where $R^9$ can be a $C_{1-8}$ alkyl group, an unsubstituted phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11-O—$(CH_2)_y$—O-group (where y can be an integer of from 1 to 3). R can also be $C_{2-12}$ alkenyl group(s), $CF_3(s)$, $CCl_3(s)$, $CH_2$ F(s), $CH_2$ Cl(s), $CHF_2(s)$, $CHCl_2(s)$, OH(s), $OR^{12}(s)$ (where $R^{12}$ can be a $C_{1-8}$ alkyl group, or a $C_{2-8}$ alkenyl group, or an aromatic group), $NR_2^{13}(s)$ (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2$ NZY where Z and Y can be, independently, H, $C_{1-4}$ alkyl, or a $C_{1-4}$ halogenated alkyl group. Preferably R can be a hydrogen, halogen, halogen containing group, an alkyl group (e.g., $C_1$-$C_{15}$ alkyl group), —$NO_2$, —OH, alkoxy, or —$NH_2$.

The amount of the starting camptothecin compound can be any desirable amount as long as sufficient acylating agent is present to convert at least a portion of the starting camptothecin to a ester of camptothecin as described herein. For example, the amount of the starting camptothecin compound can be from about 1 g to about 100 g, or more.

With respect to the acylating agent, the acylating agent generally in one or more embodiments, contains the ester group to be formed on the starting camptothecin. The acylating agent can be an organic acid derivative, such as an acid halide or acid anhydride. For instance, the acylating agent can have the formula $R^1COX^1$ or $(R^1CO)_2O$, wherein $X^1$ is a halide, such as chloride or bromide, and $R^1$ represents an organic group and generally the $R^1$ group is the group that forms the organic part of the ester attachment onto the starting camptothecin compound. More particularly, and for example purposes only, the $R^1$ group can be an alkyl group, such as a $C_1$-$C_{15}$ alkyl group, a cycloalkyl group, such as a $C_3$-$C_8$ cycloalkyl group, an alkenyl group, such as a $C_2$-$C_{15}$ alkenyl group or an epoxy group such as a $C_2$-$C_{15}$ epoxy group. Specific examples of $R^1$ groups include, but are not limited to, $CH_2CH_3$; $CH_2CH_2CH_3$; $CH_2CH_2CH_2CH_3$; $CH_2CH_2CH_2CH_2CH_2CH_3$; $CH_2CH_2CH_2CH_2CH_2$ $CH_2CH_2CH_3$; or

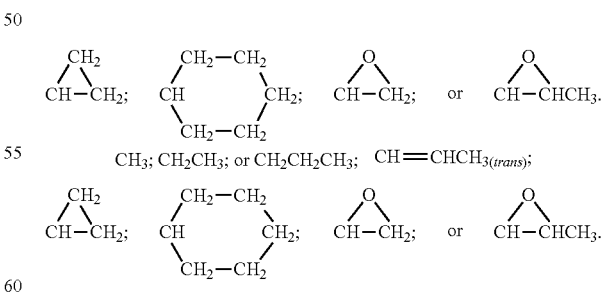

Also, for purposes of the present invention, various camptothecin esters are described below and the group identified as $R^2$ in the formula below can be the $R^1$ group in the acylating agent used in the method of the present invention. The amount of acylating agent used in the reactions of the present invention can be an amount sufficient so that an ester group is formed on the starting camptothecin compound. Suitable amounts of the acylating agent include, but are not limited to, from about 10 mL to about 1 L, based on acylating 20 g to 30 g of starting camptothecin. The examples set forth below provide exemplary amounts of the acylating agent that can be used in the reaction.

With respect to the acid used in the reactions of the present invention, the acid can be used in catalytic amounts so that the acylation of the starting camptothecin can occur with the organic acid derivatives, such as the acid halide or acid anhydride. The acid can be sulfuric acid or other acids such as HCl, $HNO_3$, or $HClO_4$. The acid can be concentrated acid such as concentrated sulfuric acid. The acid can have any molar strength, such as from about 0.0001 to about 0.02 M, or higher. The amount of acid used in the reaction can be a catalytic amount, such as from about 0.1 ml to about 1.0 ml and more preferably from about 0.20 ml to about 0.75 ml or about 0.5 ml per reaction with 20 g to 30 g of starting camptothecin. The amount of acid used to catalyze the esterification reaction can be varied depending on the scales of the reactions involved.

In the present invention, according to one or more embodiments, the various reactants can be combined together in any order, either sequentially, at the same time, or in any combination. Any reaction vessel can be used. The reaction can take place at any temperature above the freezing point of the reactants such as from about 20° C. or higher. The reaction can occur at ambient temperatures or elevated temperatures, such as from about 20° C. to about 110° C. or higher. The reaction can take place in a short order, such as from 1 minute to 1 hour or more. The reaction time depends upon the amount of reactant used, and the desirable amount of conversion of the starting CPT to camptothecin ester. The reaction can occur in inert atmospheres or in air. An example of an inert atmosphere can be a nitrogen atmosphere or argon atmosphere.

Representative examples of the esters of CPT that can be made by the methods of the present invention include the CPT esters characterized by the following formula:

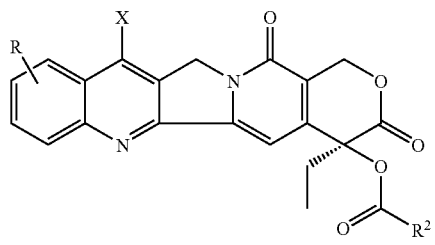

In this formula, the R group represents substituents on one of the rings of the structure above. In particular, R represents H, $NO_2$, $NH_2$, $N_3$, —OH, a halogen (e.g., F, Cl, Br, I), carboxyl (COOH), a $C_{1-16}$ alkyl group, $C_{2-16}$ alkenyl group, a $C_{3-8}$ cycloalkyl group, a $C_{1-8}$ alkoxyl group, an aroxyl group, CN, $SO_3$H, a $C_{1-8}$ halogenated alkyl group, $(CH_2)_n NR_2^7$ (where $R^7$ can be H, or a $C_{1-8}$ alkyl group, n can be an integer of from 1 to about 8), hydroxyl, SH, $SR^8$ (where $R^8$ can be a $C_{1-8}$ alkyl group, an unsubstituted phenyl group, or a substituted phenyl group), a carbonyl group, (e.g., $COR^9$, where $R^9$ can be a $C_{1-8}$ alkyl group, an unsubstituted phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11-O—$(CH_2)_y$—O-group (where y can be an integer of from 1 to 3). R can also be $C_{2-12}$ alkenyl group(s), $CF_3(s)$, $CCl_3(S)$, $CH_2 F(s)$, $CH_2 Cl(s)$, $CHF_2(s)$, $CHCl_2(s)$, OH(s), $OR^{12}(s)$ (where $R^{12}$ can be a $C_{1-8}$ alkyl group, or a $C_{2-8}$ alkenyl group, or an aromatic group), $NR_2^{13}(s)$ (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2$NZY where Z and Y can be, independently, H, $C_{1-4}$ alkyl, or a $C_{1-4}$ halogenated alkyl group. Preferably R can be a hydrogen, halogen, halogen containing group, an alkyl group (e.g., $C_1$-$C_{15}$ alkyl group), —$NO_2$, —OH, alkoxy, or —$NH_2$. $R^2$ can be an alkyl group (such as $C_1$-$C_{15}$ alkyl), a cycloalkyl group (such as a $C_2$-$C_8$ cycloalkyl), an alkenyl group (such as $C_2$-$C_{15}$ alkenyl), or an epoxy group (such as $C_1$-$C_{15}$ epoxy group).

The preferred CPT esters made by the methods of the present invention are characterized by the formula shown below:

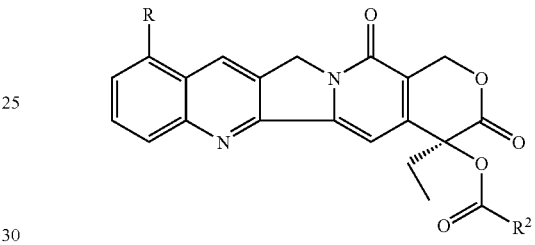

In this formula, R can be H or $NO_2$. $R^2$ represents $C_2$-$C_{15}$ alkyl group (such as a $C_2$-$C_4$ alkyl group or $C_6$-$C_{15}$ alkyl group), a $C_3$-$C_8$ cycloalkyl group, a $C_2$-$C_{15}$ alkenyl group or a $C_2$-$C_{15}$ epoxy group when R is H. When R is $NO_2$, $R^2$ is a $C_1$-$C_{15}$ alkyl group, a $C_3$-$C_8$ cycloalkyl group, a $C_2$-$C_{15}$ alkenyl group or a $C_2$-$C_{15}$ epoxy group. Preferably when R is H, $R^2$ is $CH_2CH_3$; $CH_2CH_2CH_3$; $CH_2CH_2CH_2CH_3$; $CH_2CH_2CH_2CH_2CH_2CH_3$; $CH_2CH_2CH_2CH_2CH_2CH_2CH_2CH_3$; or

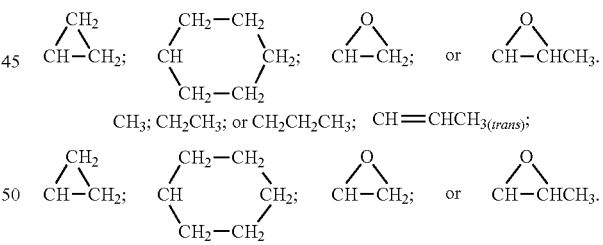

The yield of the reaction can be at least 90% or at least 90% to 99% by weight of the starting camptothecin product is converted to an ester of camptothecin. Preferably, the yield of the reaction is at least 95% of the camptothecin product to an ester of camptothecin. More preferably, the yield of the reaction is at least 99%.

The purity and/or the concentration of the starting CPT or reactant is unimportant. Different purities and different concentrations may affect the percent yield of the esters of CPT that is formed from the reaction. Preferably, the purity of the starting CPT reactant is from about 30 to about 100%. More preferably, the purity is from about 80 to about 100% or 90% to 99.9% or higher. Preferably, the amount of CPT or CPT derivative reactants is from about to 0.1 about 50%, of the total volume of the reactants. More preferably, the amount is from about to 0.5 about 5.0%, of the total volume of the reactants.

The pH, the concentration, and the purity of the acid is not important, so long as the impurities in the acid do not react with the CPT or the acylating agent. The acidity of the acid should be strong enough to he able to protonate the acylating agent employed for the reaction. Strong inorganic acids, such as $H_2SO_4$, HCl, $HNO_3$, and $HClO_4$ have this ability. Other acids, such as $AlCl_3$ and $BF_3$ can be used for this type of catalytic esterification reaction. The pH of the acid can be from about 0.5 to about 5. Preferably, the acid is concentrated and is high in purity. For example, the concentration can be from about 60 to about 100%. Preferably, the concentration is from about 95 to about 98%. The purity of the acid can be fiom about 30 to about 100%. Preferably, the purity is from about 90 to about 100%. Preferably, the amount of acid, such as concentrated sulfuric acid, is from about 0.1 to about 10%, of the total volume of the reactants. More preferably, the amount is from about 0.5 to about 8.5%, of the total volume of the reactants.

Preferably, the acid is added to the mixture of the CPT and the acyl halide while the mixture is being stirred. Preferably, the amount of acid that can be added to the mixture is sufficient for the acid to act as a catalyst. Preferably, about 4 to about 8 glass pipet drops of the acid can be added to about 70-100 ml of the acyl halide (A similar amount of acid can be used when the acylating agent is other than the acyl halide). However, if necessary, more or less acid can be added to the mixture of the CPT and the acyl halide, preferably while the mixture is being stirred.

The mixture of CPT, acyl halide and acid can be placed in a reactor, which preferably includes an inert atmosphere, such as $N_2$, and can be heated from about 80° C. to about 120° C. Preferably, the mixture is heated from about 90° C. to about 110° C. and more preferably, the reactor is heated to about 100° C.

Preferably, the reaction will run until the desired product is formed. The reaction time can be as short as several hours to as long as several days. Preferably, the reaction time can be about 15 hours under an inert atmosphere, such as $N_2$.

An example of the reaction is depicted in Scheme 1 below.

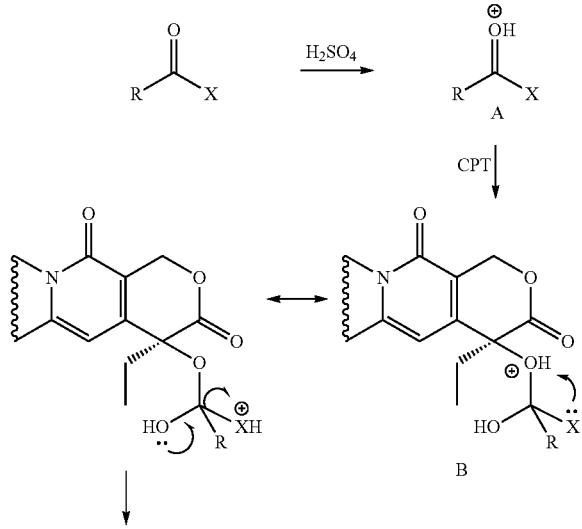

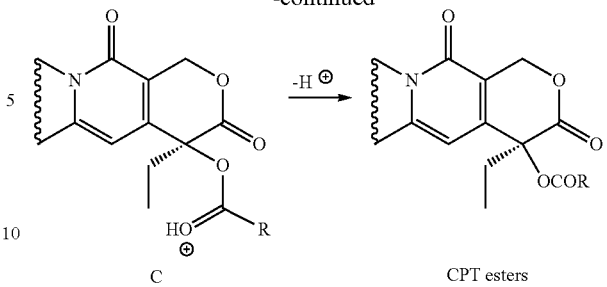

While not wishing to be bound by any theory, it is believed that the protonation of the acylating agent (RCOX) with an acid, such as sulfuric acid, forms a reactive intermediate A. Attaching a cationic carbonyl carbon of intermediate A with camptothecin forms an intermediate B. The subsequent elimination of a molecule of XH from B gives final ester products.

After completion of the reaction, which can be determined by a change in the color of the solution, the solution can be cooled to room temperature. The solvent can be removed by any commonly known separation methods, such as an evaporation method or a filtration method. The crude product obtained after removing the reaction solvents can be purified by refluxing in alcoholic solvents, such as ethanol. The final product is obtained in crystalline form upon recrystallization and/or reprecipitation from the alcohol.

The present invention will be further clarified by the following examples, which are intended to be purely exemplary of the present invention.

EXAMPLES

Example 1

Camptothecin-20-propionate (CZ48) was prepared as follows.

20 g camptothecin (0.05747 mole) and 100 ml propionic anhydride (97%, Aldrich Chemical Co., Milwaukee, Wis.) were added to a 200 ml round-bottomed flask equipped with a magnetic stirrer and a sand bath. The mixture was heated by sand bath while stirring. A few drops (8 to 10) of concentrate sulfuric acid (95-98%, A.C.S. reagent, Aldrich Chemical Co.) were added drop by drop when the sand bath temperature reached 80° C. The mixture was then stirred at 110±10° C. for overnight (~14 hr). After cooling down to room temperature, the reaction mixture was poured onto 1000 ml ice water portion by portion while stirring. After stirring for roughly 45 min, the mixture was filtrated. The residue obtained from filtration was allowed air-drying for 24 hr. The dried crude product was transferred to a 500 ml round-bottomed flask equipped with a heating mantle.

To this crude product was added 200 ml absolute ethanol (99.5%, 200 proof, Aldrich Chemical Co.). The mixture was allowed to reflux for 2 hr, and then cooled to room temperature. The pure product was obtained as crystals after crystallization from ethanol. Purity was shown to be 99.8%, using high performance liquid chromatography (HPLC), and the melting point (mp) was determined to be 242° C. Thin layer chromatography (TLC) showed the identical $R_f$ (Retention factor) values with the authentic camptothecin-20-propionate prepared in the laboratory previously. The proton Nuclear Magnetic Resonance (NMR) also showed the identical spectrum with the authentic sample.

Example 2

With the same procedure as in Example 1, all listed products in Table 1, as shown below, were prepared by using the corresponding organic acid anhydride or chloride as acylating agents. The yields of the reaction for the products are shown in Table 1.

Dry nitrogen was routinely used as the reaction atmosphere in all reactions for the preparations shown in Table 1. All glasswares were baked at 70±10° C. for a minimum of 2 h before being used. Melting points were obtained with a MEL-TEMP® melting point apparatus and were uncorrected. Camptothecin was purchased from The People's Republic of China and used as purchased. Nine nitrocamptothecins were prepared in the laboratory by using an established procedure as set forth by Cao et al., *Synthesis* 1998, 1724, and is incorporated herein in its entirety.

With excessive organic acid derivatives, such as acid chloride (or bromide) and acid anhydrides, as acylating agents, and reaction media, camptothecin was allowed to react with them at room temperature or at an elevated temperature under $N_2$ atmosphere with a few drops of concentrated sulfuric acid as a catalyst. After subsequent preparation, camptothecin ester products were obtained in high yields. Table 1 shows the comparison of the reaction yields of 13 camptothecin esters between the $H_2SO_4$-catalyzed acylation procedure according to the present invention and the literature reported procedures. As shown in Table 1, camptothecin-20-propionate, butyrate, valerate, and heptanoate were all obtained in high reaction yields.

The conventional anhydrides/pyridine procedure was frequently used in preparing ester compounds and usually gave high reaction yields when the corresponding anhydrides were available. However, organic anhydrides were not always available. For example, nonanoyl chloride as an acylating agent was used rather than the corresponding anhydride when preparing camptothecin-20-nonanoate. In this situation, the reaction yield of the product was only 6% (conventional procedure).

For the preparations of the Table 1-listed CPT esters using another conventional procedure, the DCC/DMAP procedure, as previously described, did not work. Three reactions with this procedure were attempted. All of them failed to give the expected CPT esters, and the starting camptothecin materials were 100% recovered.

However, the $H_2SO_4$-catalyzed acylation of camptothecin derivatives with the corresponding acid anhydrides or chlorides according to the present invention, gave high yields for every reaction as shown in Table 1. When nonanoyl chloride was employed as an acylating agent, the $H_2SO_4$-catalyzed reaction gave camptothecin-20-nonanoate in 92% yield while the previously reported method in the literatures only gave 6%.

TABLE 1

Comparison of reaction yields of $H_2SO_4$-catalyzed esterification of camptothecin with prevously reported procedure

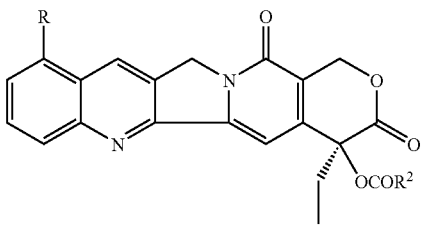

| | | Reaction yields (%) | |
|---|---|---|---|
| $R^2$ | R | Previously reported | $H_2SO_4$-catalyzed |
| $CH_3$ | H | 58 | 96 |
| $C_2H_5$ | H | 94 | 99 |
| $C_3H_7$ | H | 92 | 98 |
| $C_4H_9$ | H | 90 | 99 |
| $C_6H_{13}$ | H | 98 | 99 |
| $C_8H_{17}$ | H | 6 | 92 |
| $CH=CHCH_3$ | H | 31 | 90 |
| $CH_3$ | $NO_2$ | 45 | 98 |
| $C_2H_5$ | $NO_2$ | 73 | 99 |
| $C_3H_7$ | $NO_2$ | 56 | 98 |
| $C_4H_9$ | $NO_2$ | 82 | 97 |
| $C_6H_{13}$ | $NO_2$ | 88 | 95 |
| $i$-$C_3H_7$ | $NO_2$ | 14 | 92 |

Thus, the $H_2SO_4$-catalyzed procedure provided an efficient way for preparing camptothecin esters. As shown above, the yields of the final products in the synthetic pathways according to the present invention, typically was above 90% depending on the exact reaction conditions, the purity of the starting materials, the nature of the acylating agent, the type of acid or base, and other factors or parameters common in synthetic organic chemistry. The methods of producing the compounds of the present invention, as set forth above, are not meant to be exclusive or limiting, but rather are exemplary only, and other means for generating these compounds, or optimizing the reaction conditions are possible for persons skilled in the art.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of making an aliphatic ester of camptothecin comprising reacting a starting camptothecin compound with at least one acylating agent and at least one acid that is concentrated acid, wherein said at least one acid is present in a catalytic amount and said at least one acylating agent is protonated by said at least one acid and said starting camptothecin compound is 20(S)-camptothecin, 9-nitro-camptothecin, or 9-aminocamptothecin, and said acylating agent has the formula $(R^1CO)_2O$, wherein $R^1$ represents $CH_3$; $C_2H_5$; $C_3H_7$; $C_4H_9$; $C_6H_{13}$; $C_8H_{17}$; or $CH=CHCH_3$; and wherein at least 90% by weight of said starting camptothecin compound is converted to said aliphatic ester of camptothecin.

2. The method of claim 1, wherein said at least one acid is sulfuric acid.

3. The method of claim 1, wherein said starting camptothecin compound is 20(S)-camptothecin.

4. The method of claim 1, wherein said starting camptothecin compound is 20(S)-camptothecin and said $R^1$ is $C_2H_5$.

5. The method of claim 4, wherein said acid is sulfuric acid.

6. The method of claim 5, wherein said acid is concentrated HCl, concentrated $HNO_3$, or concentrated $HClO_4$.

7. The method of claim 1, wherein at least 95% by weight of said starting camptothecin compound is converted to said aliphatic ester of camptothecin.

8. The method of claim 1, wherein at least 99% by weight of said starting camptothecin compound is converted to said aliphatic ester of camptothecin.

9. The method of claim 1, wherein said starting camptothecin compound is 9-nitro-camptothecin.

10. The method of claim 1, wherein said starting camptothecin compound is 9-aminocamptothecin.

11. The method of claim 1, wherein said starting camptothecin compound is 20(S)-camptothecin and $R^1$ is $CH_3$, $C_8H_{17}$, or $CH=CHCH_3$.

* * * * *

UNITED STATES PATENT AND TRADEMARK OFFICE
CERTIFICATE OF CORRECTION

PATENT NO. : 7,928,235 B2
APPLICATION NO. : 11/833031
DATED : April 19, 2011
INVENTOR(S) : Cao It is certified that error appears in the above-identified patent and that said Letters Patent is hereby corrected as shown below:

IN THE CLAIMS:

Column 14, line 2, in Claim 6, "claim 5" should read -- claim 1 --.

Signed and Sealed this
Fourteenth Day of June, 2011

David J. Kappos
*Director of the United States Patent and Trademark Office*